(12) United States Patent
Ishihara et al.

(10) Patent No.: US 10,765,633 B2
(45) Date of Patent: Sep. 8, 2020

(54) FORMULATION COMPRISING LIPOSOMES

(71) Applicant: Eisai R&D Management Co., Ltd., Tokyo (JP)

(72) Inventors: Hiroshi Ishihara, Tsukuba (JP); Katsura Hata, Tsukuba (JP); Hiroki Muto, Tsukuba (JP); Geoff Hird, Chapel Hill, NC (US)

(73) Assignee: EISAI R&D MANAGEMENT CO., LTD, Tokyo (JP)

( * ) Notice: Subject to any disclaimer, the term of this patent is extended or adjusted under 35 U.S.C. 154(b) by 0 days.

(21) Appl. No.: 16/713,027

(22) Filed: Dec. 13, 2019

(65) Prior Publication Data

US 2020/0188300 A1 Jun. 18, 2020

Related U.S. Application Data

(60) Provisional application No. 62/780,642, filed on Dec. 17, 2018.

(51) Int. Cl.
*A61K 9/127* (2006.01)
*A61K 47/10* (2017.01)
*A61K 31/7024* (2006.01)

(52) U.S. Cl.
CPC .......... *A61K 9/1271* (2013.01); *A61K 9/1277* (2013.01); *A61K 31/7024* (2013.01); *A61K 47/10* (2013.01)

(58) Field of Classification Search
CPC .... A61K 9/1271; A61K 9/1277; A61K 47/10; A61K 31/7024; A61K 9/127; A61K 31/7034
See application file for complete search history.

(56) References Cited

U.S. PATENT DOCUMENTS

| | | | |
|---|---|---|---|
| 5,530,113 A | 6/1996 | Christ et al. | |
| 5,681,824 A | 10/1997 | Christ et al. | |
| 5,750,664 A | 5/1998 | Christ et al. | |
| 5,935,938 A | 8/1999 | Christ et al. | |
| 6,184,366 B1 | 2/2001 | Christ et al. | |
| 6,906,042 B2 | 6/2005 | McShane et al. | |
| 2005/0129750 A1* | 6/2005 | Hu | A61K 9/1271 424/450 |
| 2006/0222655 A1 | 10/2006 | McShane | |
| 2013/0156845 A1* | 6/2013 | Manoharan | C12N 15/111 424/450 |
| 2014/0105827 A1* | 4/2014 | Morse | C12Q 1/6886 424/9.34 |

(Continued)

FOREIGN PATENT DOCUMENTS

| | | |
|---|---|---|
| WO | 96/39411 A1 | 12/1996 |
| WO | 2012/047656 A1 | 4/2012 |
| WO | 2018/181963 A1 | 10/2018 |

OTHER PUBLICATIONS

Raja, S.G., et al in Core Evid., 2 (3), pp. 199-207, 2007.*

(Continued)

*Primary Examiner* — Gollamudi S Kishore
(74) *Attorney, Agent, or Firm* — Buchanan Ingersoll & Rooney PC

(57) ABSTRACT

A formulation comprising liposomes, wherein the liposomes comprise, based on the liposome, 0.7 to 3.0 mol % of eritoran or a pharmaceutically acceptable salt thereof and 0.5 to 3.0 mol % of a PEGylated phospholipid.

21 Claims, 3 Drawing Sheets

(56) References Cited

U.S. PATENT DOCUMENTS

| | | | | |
|---|---|---|---|---|
| 2014/0199233 | A1* | 7/2014 | Nagy | A61K 9/1273 424/1.11 |
| 2014/0302120 | A1* | 10/2014 | Carson | A61K 47/6911 424/450 |
| 2016/0024498 | A1* | 1/2016 | Fitzgerald | C12N 15/111 424/450 |
| 2020/0016079 | A1 | 1/2020 | Kasagi et al. | |

OTHER PUBLICATIONS

Tidswell M. et al in Crit. Care Med. 38 (1) pp. 72-83 Jan. 2010.*
Horber et al., "Pharmacokinetic Properties and Interactions with Blood Components of N4-Hexadecyl-1-β-D-arabinofuranosylcytosine (NHAC) Incorporated into Liposomes," Journal of Pharmacy and Pharmacology, (Apr. 1995), vol. 47, Issue 4, pp. 282-288.
Panagi et al., "Protein-induced CF release from liposomes in vitro and its correlation with the Blood/RES biodistribution of liposomes," International Journal of Pharmaceutics, (Mar. 1998), No. 163, Issue 1-2, pp. 103-114.
Park et al., "Distribution Within the Organs of a Reticuloendothelial System of Liposomes Containing Lipid A," Journal of Drug Targeting, (1993), vol. I, Issue 4, pp. 325-330.
Notification of Transmittal of the International Search Report (Forms PCT/ISA/220 and PCT/ISA/210) and the Written Opinion of the International Searching Authority (Form PCT/ISA/237) dated Feb. 18, 2020, by the Japan Patent Office in corresponding International Application No. PCT/JP2019/048842. (11 pages).
Rossignol et al., "Safety, Pharmacokinetics, Pharmacodynamics, and Plasma Lipoprotein Distribution of Eritoran (E5564) during Continuous Intravenous Infusion into Healthy Volunteers", Antimicrobial Agents and Chemotherapy, Sep. 2004, pp. 3233-3240, vol. 48, No. 9, American Society for Microbiology.

* cited by examiner

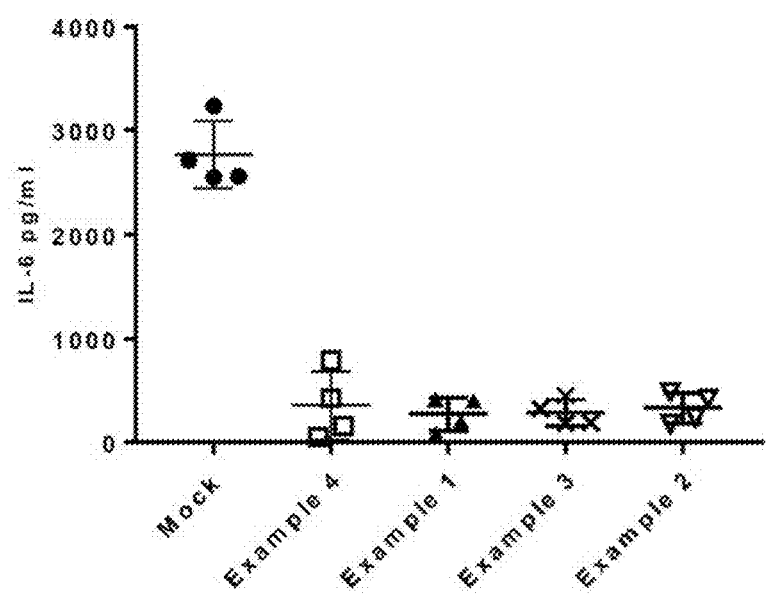
[Fig. 1]

[Fig. 2-1]
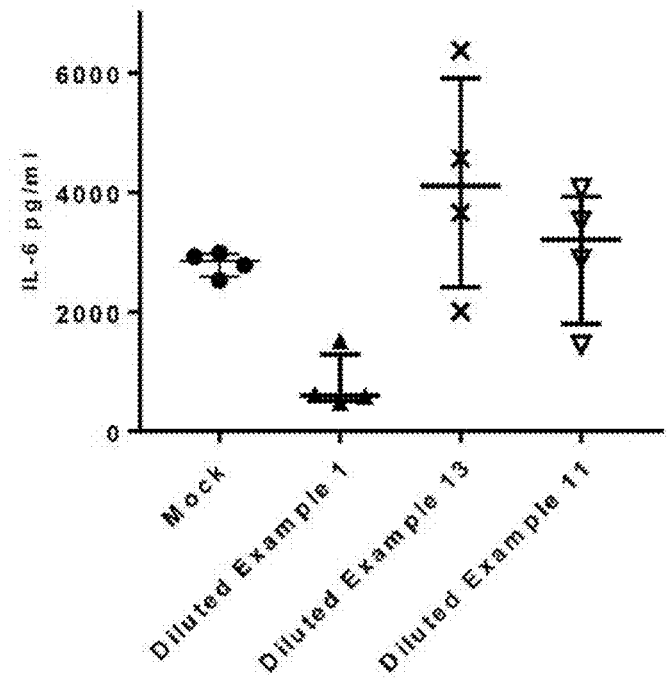
[Fig. 2-2]
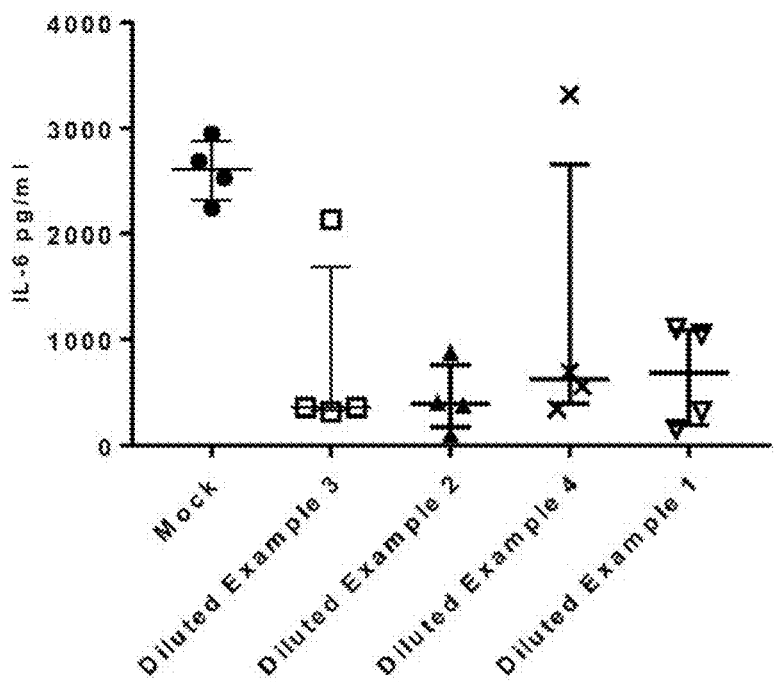

[Fig. 2-3]
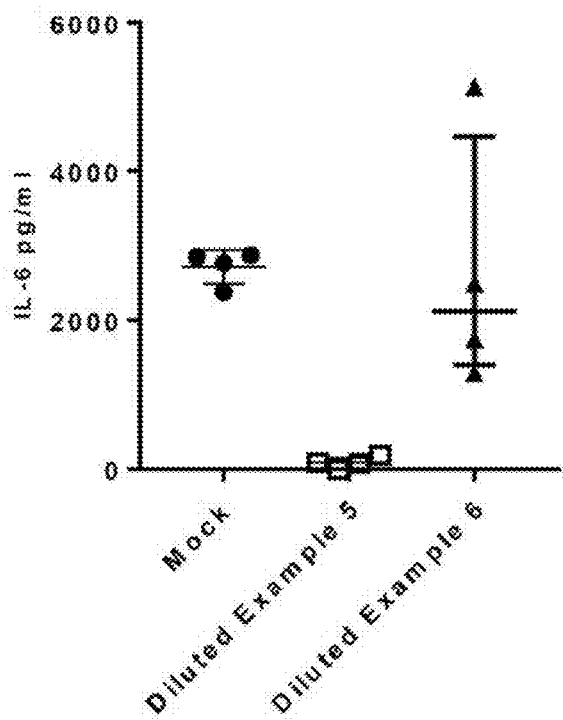
[Fig. 3]
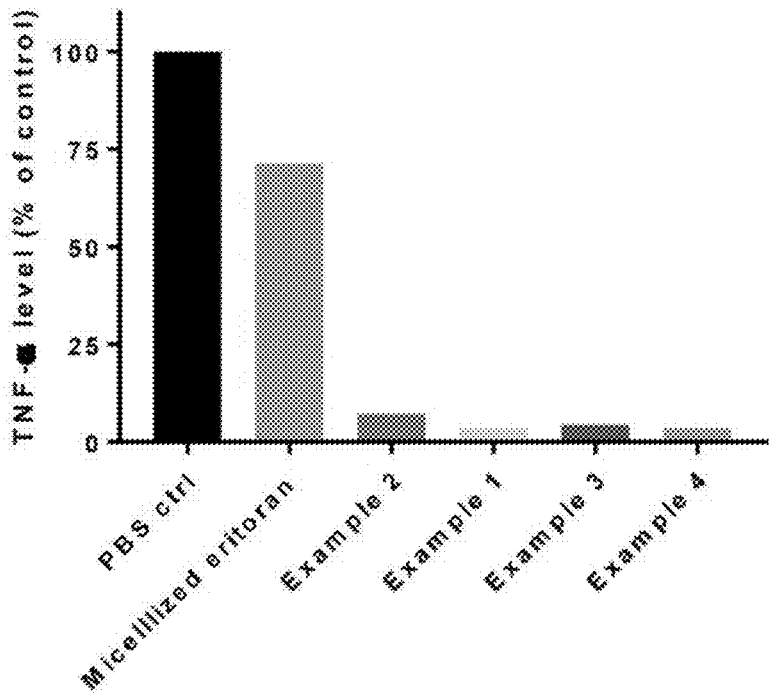

FORMULATION COMPRISING LIPOSOMES

FIELD OF THE INVENTION

The present disclosure relates to a formulation comprising liposomes.

BACKGROUND

Eritoran, which is also referred to as "E5564", is a lipopolysaccharide analog comprising two sugar moieties and four long chain fatty acid moieties. Eritoran has a molecular weight of about 1,401. Methods for preparing eritoran are described in U.S. Pat. Nos. 5,530,113; 5,681,824; 5,750,664; 5,935,938; and 6,184,366, and in WO 96/39411. Those documents are incorporated by reference herein. Eritoran drug formulations with varying micelle hydrodynamic diameters have reportedly been achieved by controlling pH and concentration of counter-ions in a solution. That is reported in U.S. Pat. No. 6,906,042, which is incorporated by reference herein.

Eritoran is a Lipid A analog that acts as a Toll-like receptor 4 (TLR4) antagonist. Eritoran has the following structure:

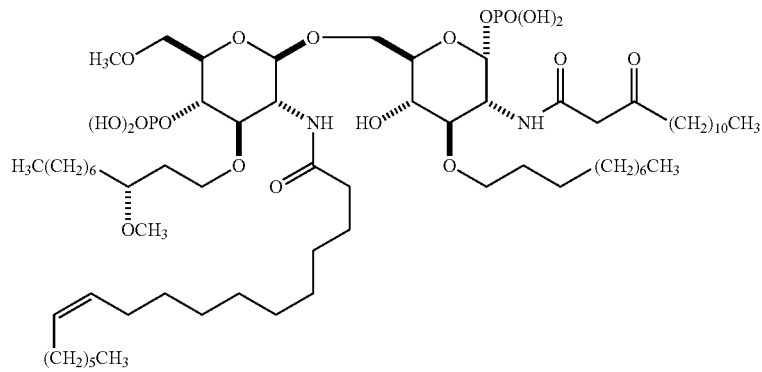

The activity of Lipid A analogs has been reported to be altered by interactions with lipoprotein cholesterol. These lipoproteins are typically present in human serum and include low-density lipoproteins (LDLs) and high-density lipoproteins (HDLs). A study has postulated that changes in plasma lipoprotein profiles can alter both efficacy and pharmacodynamics profiles of lipophilic drugs. In particular, the study noted that binding of eritoran to HDL resulted in time-dependent loss of drug activity. See Daniel P. Rossignol, et al., "Safety, Pharmacokinetics, Pharmacodynamics, and Plasma Lipoprotein Distribution of Eritoran (E5564) during Continuous Intravenous Infusion into Healthy Volunteers" *Antimicrobial Agents & Chemotherapy*, September 2004, p. 3233-3240, which is incorporated by reference herein.

SUMMARY

One of the objects of the present disclosure is to provide an eritoran-containing formulation which has higher activities in vivo or in the presence of HDL (e.g. human HDL), preferably interleukin-6 (IL-6) generation-inhibiting activities or TNF-α generation-inhibiting activities, than eritoran itself or micellized eritoran. The present inventors have found that a liposome comprising eritoran and a PEGylated phospholipid has higher activities in vivo or in the presence of HDL (e.g. human HDL) and that adjusting the amounts of eritoran and a PEGylated phospholipid enables the liposome to have much higher activities.

The present disclosure provides the following embodiments.

[1] A formulation comprising liposomes, wherein the liposomes comprise, based on the liposome, 0.7 to 3.0 mol % of eritoran or a pharmaceutically acceptable salt thereof and 0.5 to 3.0 mol % of a PEGylated phospholipid.

[2] The formulation according to [1], wherein the pharmaceutically acceptable salt is tetrasodium salt.

[3] The formulation according to [1] or [2], wherein the liposomes comprise, based on the liposome, 1.0 to 2.5 mol % of eritoran or a pharmaceutically acceptable salt thereof and 1.0 to 2.5 mol % of a PEGylated phospholipid.

[3-1] The formulation according to any one of [1] to [3], wherein the liposomes comprise, based on the liposome, 1.0 mol % of eritoran or a pharmaceutically acceptable salt thereof and 1.0 mol % of a PEGylated phospholipid.

[3-2] The formulation according to any one of [1] to [3], wherein the liposomes comprise, based on the liposome, 1.0 mol % of eritoran or a pharmaceutically acceptable salt thereof and 2.5 mol % of a PEGylated phospholipid.

[3-3] The formulation according to any one of [1] to [3], wherein the liposomes comprise, based on the liposome, 2.5 mol % of eritoran or a pharmaceutically acceptable salt thereof and 1.0 mol % of a PEGylated phospholipid.

[3-4] The formulation according to any one of [1] to [3], wherein the liposomes comprise, based on the liposome, 2.5 mol % of eritoran or a pharmaceutically acceptable salt thereof and 2.5 mol % of a PEGylated phospholipid.

[4] The formulation according to any one of [1] to [3], wherein the PEGylated phospholipid is 1,2-distearoyl-sn-glycero-3-phosphoethanolamine-N-[methoxy(polyethylene glycol)-2000].

[5] The formulation according to [4], wherein the liposomes comprise, based on the liposome, 1.0 mol % of eritoran or a pharmaceutically acceptable salt thereof and 1.0 mol % of 1,2-distearoyl-sn-glycero-3-phosphoethanolamine-N-[methoxy(polyethylene glycol)-2000].

[6] The formulation according to [4], wherein the liposomes comprise, based on the liposome, 1.0 mol % of eritoran or a pharmaceutically acceptable salt thereof and 2.5 mol % of 1,2-distearoyl-sn-glycero-3-phosphoethanolamine-N-[methoxy(polyethylene glycol)-2000].

[7] The formulation according to [4], wherein the liposomes comprise, based on the liposome, 2.5 mol % of eritoran or a pharmaceutically acceptable salt thereof and 1.0 mol % of 1,2-distearoyl-sn-glycero-3-phosphoethanolamine-N-[methoxy(polyethylene glycol)-2000].

[8] The formulation according to [4], wherein the liposomes comprise, based on the liposome, 2.5 mol % of eritoran or a pharmaceutically acceptable salt thereof and 2.5 mol % of 1,2-distearoyl-sn-glycero-3-phosphoethanolamine-N-[methoxy(polyethylene glycol)-2000].

[9] The formulation according to any one of [1] to [8], wherein the liposomes further comprise a phosphatidylcholine.

[10] The formulation according to [9], wherein the phosphatidylcholine is distearoyl phosphatidyl choline.

[11] The formulation according to any one of [1] to [10], wherein the liposomes further comprise an antioxidant.

[12] The formulation according to [11], wherein the antioxidant is butylated hydroxyanisole.

[13] The formulation according to any one of [1] to [12], wherein the liposomes further comprise, based on the liposome, 0 to 10 mol % of a sterol.

[14] The formulation according to [13], wherein the sterol is cholesterol.

[15] The formulation according to [13], wherein the liposomes do not comprise the sterol.

[16] The formulation according to any one of [1] to [15], wherein the liposomes have an average particle size between 100 to 120 nm, as measured by Dynamic Light Scattering (DLS).

[17] The formulation according to any one of [1] to [16], wherein the liposomes have a polydispersity index of 0.20 or less.

[18] A method for producing a formulation comprising liposomes, comprising:
  preparing a solution comprising, based on all components of the liposomes to be used, 0.7 to 3.0 mol % of eritoran or a pharmaceutically acceptable salt thereof, 0.5 to 3.0 mol % of a PEGylated phospholipid and a solvent;
    evaporating the solvent from the solution to form a thin film;
    dispersing the thin film in a buffer solution to form a liquid dispersion; and
    extruding the liquid dispersion through a filter to form the formulation.

[19] The method according to [18], wherein the solution further comprises a phosphatidylcholine and an antioxidant.

[20] The method according to [18] or [19], wherein the solvent is a combination of chloroform and methanol.

[21] The method according to any one of [18] to [20], wherein the dispersing step is performed by sonication.

[22] The method according to any one of [18] to [21], wherein the method further comprises adjusting the pH of the formulation formed in the extruding step to 6.2 to 6.8.

The present disclosure further provides the following embodiments.

[A] The formulation according to any one of embodiments [1] to [22] for use in the inhibition of binding of lipopolysaccharides to TLR4, for use in the inhibition of TLR4 dimerization, for use in the inhibition of TLR4 signaling, for use in the inhibition of IL-6 generation, for use in the treatment or prevention of diseases which are mediated through the activation of TLR4 or the generation of IL-6, for use in the inhibition of TNF-α generation, or for use in the treatment or prevention of diseases which are mediated through the generation of TNF-α.

[B] A method for the inhibition of binding of lipopolysaccharides to TLR4, for the inhibition of TLR4 dimerization, for the inhibition of TLR4 signaling, for the inhibition of IL-6 generation, for the treatment or prevention of diseases which are mediated through the activation of TLR4 or the generation of IL-6, for use in the inhibition of TNF-α generation, or for use in the treatment or prevention of diseases which are mediated through the generation of TNF-α, comprising administering an effective amount of the formulation according to any one of embodiments [1] to [22] to a subject in need thereof.

[C] Use of the formulation according to any one of embodiments [1] to [22] for the inhibition of binding of lipopolysaccharides to TLR4, for the inhibition of TLR4 dimerization, for the inhibition of TLR4 signaling, for the inhibition of IL-6 generation, for the treatment or prevention of diseases which are mediated through the activation of TLR4 or the generation of IL-6, for use in the inhibition of TNF-α generation, or for use in the treatment or prevention of diseases which are mediated through the generation of TNF-α.

[D] Use of the formulation according to any one of embodiments [1] to [22] in the manufacture of a medicament for the inhibition of binding of lipopolysaccharides to TLR4, for the inhibition of TLR4 dimerization, for the inhibition of TLR4 signaling, for the inhibition of IL-6 generation, for the treatment or prevention of diseases which are mediated through the activation of TLR4 or the generation of IL-6, for use in the inhibition of TNF-α generation, or for use in the treatment or prevention of diseases which are mediated through the generation of TNF-α.

As to embodiments [A] to [D], features described in the below section <Formulation> can be referred to.

According to the present disclosure, an eritoran-containing formulation which has higher activities in vivo or in the presence of HDL (e.g. human HDL), preferably IL-6 generation-inhibiting activities or TNF-α generation-inhibiting activities, than eritoran itself or micellized eritoran can be provided.

BRIEF DESCRIPTION OF DRAWINGS

FIG. 1 shows in vivo IL-6 generation-inhibiting activity of the formulations of Examples 1 to 4.

FIG. 2-1 shows in vivo IL-6 generation-inhibiting activity of the formulations of Diluted Examples 1, 11 and 13.

FIG. 2-2 shows in vivo IL-6 generation-inhibiting activity of the formulations of Diluted Examples 1 to 4.

FIG. 2-3 shows in vivo IL-6 generation-inhibiting activity of the formulations of Diluted Examples 5 and 6.

FIG. 3 shows TNF-α generation-inhibiting activity of micellized eritoran and the formulations of Examples 1 to 4 in the presence of human HDL.

DETAILED DESCRIPTION

Definition

As used herein, the articles "a" and "an" mean "one or more" or "at least one" unless otherwise indicated.

<Formulation>

One embodiment relates to a formulation comprising liposomes, wherein the liposomes comprise, based on the liposome, 0.7 to 3.0 mol % of eritoran or a pharmaceutically acceptable salt thereof and 0.5 to 3.0 mol % of a PEGylated phospholipid. It has been found that liposomes comprising a lower amount of eritoran or a pharmaceutically acceptable salt thereof have higher activities in vivo or in the presence of HDL (e.g. human HDL).

The formulation may comprise, in addition to the liposomes, lipid bilayer discs. The formulation may comprise, in addition to the liposomes, lipid bilayers. The formulation may comprise, in addition to the liposomes, the lipid bilayer discs and the lipid bilayers. As used herein, the lipid bilayer forms neither a liposome nor a lipid bilayer disc.

The liposomes comprise eritoran or a pharmaceutically acceptable salt thereof. The term "pharmaceutically acceptable salt" is well known in the art. Examples of the pharmaceutically acceptable salt include, but not limited to, alkali metal salts, e.g., lithium, sodium or potassium salts; and alkaline earth metal salts, e.g., calcium or magnesium salts. The pharmaceutically acceptable salt of eritoran is preferably sodium salt, e.g., tetrasodium salt.

The amount of the eritoran or a pharmaceutically acceptable salt thereof contained in the liposome is 0.7 to 3.0 mol %, preferably 1.0 to 2.5 mol %, based on the liposome. Adjusting the amount of the eritoran or a pharmaceutically acceptable salt thereof within the above range or to the above point enables the formulation to have much higher activities.

The liposomes comprise a PEGylated phospholipid. The PEGylated phospholipid has a polyethylene glycol ("PEG") moiety covalently bonded to a phospholipid. The molecular weight of the PEG group is preferably about 500 to about 5,000, more preferably about 1,000 to about 3,000, and still more preferably about 2,000. The PEGylated phospholipid has preferably acyl groups having 14 to 18 carbon atoms, and more preferably acyl groups having 18 carbon atom. Examples of the PEGylated phospholipid include, but not limited to, 1,2-distearoyl-sn-glycero-3-phosphoethanolamine-N-[methoxy(polyethylene glycol)-2000] (DSPE-PEG2000), and 1,2-dimyristoyl-sn-glycero-3-phosphoethanolamine-N-[methoxy(polyethylene glycol)-2000] (DMPE-PEG2000). These PEGylated phospholipids may be used alone or in combination. The PEGylated phospholipid is preferably DSPE-PEG2000 having the following structure:

2.5 mol %, 2.5 mol % and 1.0 mol %, or 2.5 mol % and 2.5 mol %, respectively, based on the liposome.

The liposomes may further comprise a phosphatidylcholine. Examples of the phosphatidylcholine include, but not limited to, Soy PC, Egg PC, dielaidoyl phosphatidyl choline (DEPC), dioleoyl phosphatidyl choline (DOPC), distearoyl phosphatidyl choline (syn. 1,2-distearoyl-sn-glycero-3-phosphocholine) (DSPC), hydrogenated soybean phosphatidyl choline (HSPC), dipalmitoyl phosphatidyl choline (DPPC), 1-palmitoyl-2-oleo phosphatidyl choline (POPC), dibehenoyl phosphatidyl choline (DBPC), and dimyristoyl phosphatidyl choline (DMPC). These phosphatidylcholines may be used alone or in combination. The phosphatidylcholine is preferably DSPC having the following structure:

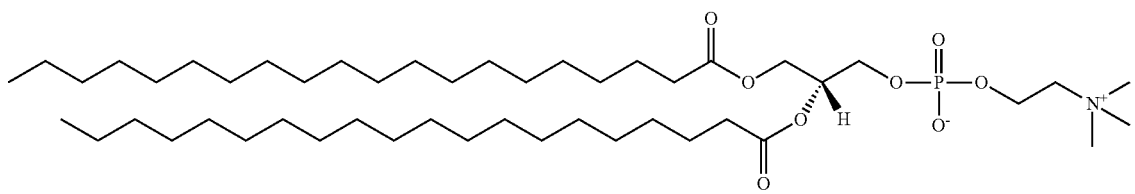 [SMILES: CCCCCCCCCCCCCCCCCCCC(=O)OC[C@H](COP(=O)([O-])OCC[N+](C)(C)C)OC(=O)CCCCCCCCCCCCCCCCCCC]

The term "Soy-PC" refers to a phosphatidyl choline composition comprising a variety of mono-, di-, tri-unsaturated and saturated fatty acids. Typically, Soy-PC comprises palmitic acid in an amount of about 12% to about 33% by weight, stearic acid in an amount of about 3% to about 8% by weight, oleic acid in an amount of about 4% to about 22% by weight, linoleic acid in an amount of about 60% to about 66% by weight, and linolenic acid in an amount of about 5% to about 8% by weight.

The term "Egg-PC" refers to a phosphatidyl choline composition comprising a variety of saturated and unsaturated fatty acids. Typically, Egg-PC comprises palmitic acid in an amount of about 34% by weight, stearic acid in an amount of about 10% by weight, oleic acid in an amount of about 31% by weight, and linoleic acid in an amount of about 18% by weight.

The amount of the phosphatidylcholine contained in the liposome is preferably 86 to 98 mol %, more preferably 89 to 97 mol %, and still more preferably 92 to 96 mol %, based on the liposome.

The liposomes may further comprise an antioxidant. Examples of the antioxidant include, but not limited to,

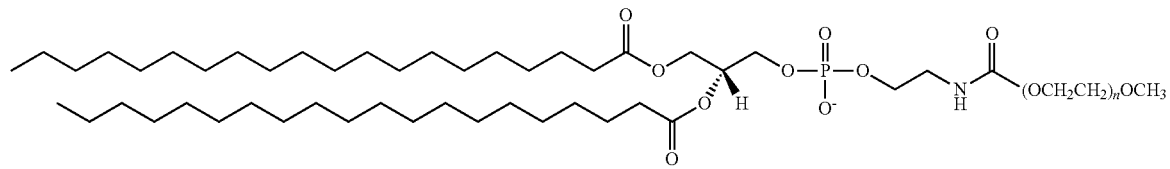

($n = 45$)

The amount of the PEGylated phospholipid contained in the liposome is 0.5 to 3.0 mol %, preferably 1.0 to 2.5 mol %, based on the liposome. Adjusting the amount of the PEGylated phospholipid within the above range or to the above point enables the formulation to have much higher activities.

Preferably, the amount of the eritoran or a pharmaceutically acceptable salt thereof and the PEGylated phospholipid in the liposome is 1.0 mol % and 1.0 mol %, 1.0 mol % and butylated hydroxyanisole (BHA), butylated hydroxytoluene, ascorbic acid, ascorbate sodium, ascorbyl palmitate, sulfite sodium, bisulfate sodium, cysteinate hydrochloride, dithionate sodium, glutamate monosodium, glutathione, propyl gallate, tocopherol alpha, alpha tocopherol hydrogen succinate, and ethylene diamine tetra acetic acid salts. These antioxidants may be used alone or in combination. The antioxidant is preferably BHA.

The amount of the antioxidant contained in the liposome is preferably 0.02 to 0.12 mol %, more preferably 0.04 to 0.10 mol %, and still more preferably 0.06 to 0.08 mol %, based on the liposome.

The liposomes may further comprise a sterol. Examples of the sterol include, but not limited to, cholesterol, campesterol, β-sitosterol, stigmasterol, and ergosterol. These sterols may be used alone or in combination. The sterol is preferably cholesterol having the following structure:

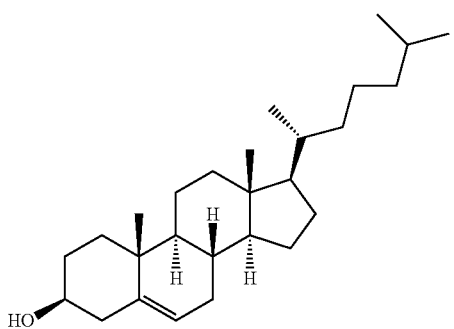

The amount of the sterol contained in the liposome is preferably 0 to 30 mol %, more preferably 0 to 10 mol %, still more preferably 0 to 6 mol %, and the most preferably 0%, based on the liposome. Reducing the amount of the sterol enables the formulation to have much higher activities.

Preferably, the liposomes only consists of eritoran or a pharmaceutically acceptable salt thereof, the PEGylated phospholipid, the phosphatidylcholine and the antioxidant. More preferably, the liposomes only consists of eritoran or a pharmaceutically acceptable salt thereof, 1,2-distearoyl-sn-glycero-3-phosphoethanolamine-N-[methoxy(polyethylene glycol)-2000], distearoyl phosphatidyl choline and butylated hydroxyanisole. Employing these components enables the formulation to have much higher activities. It would be understood by a person skilled in the art that the liposomes can include materials such as water and buffer within their internal space.

The components of the liposome and the amount thereof, which are described above, can be applied to the lipid bilayer discs and the lipid bilayers.

The formulation may further comprise optional components. Examples of the optional component include, but not limited to, pharmaceutically acceptable excipients such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose and polyacrylic acids; lubricating agents such as talc, magnesium stearate and mineral oil; wetting agents; emulsifying agents; suspending agents; preserving agents such as methyl-, ethyl-, and propyl-hydroxybenzoates; pH adjusting agents such as inorganic and organic acids and bases; sweetening agents; and flavoring agents.

Although the average particle size of the liposomes can be appropriately adjusted by a commonly known method, the liposomes have an average particle size (Z-ave) preferably between 80 to 140 nm, and more preferably between 100 to 120 nm, as measured by Dynamic Light Scattering (DLS).

The liposomes have a polydispersity index (PdI) preferably of 0.20 or less, more preferably of 0.10 or less, and still more preferably of 0.05 or less. Although the lower limit of PdI is not particularly limited, it is, for example, 0.01.

The formulation may be used to inhibit binding of lipopolysaccharides (LPSs) to TLR4. The formulation may be used to inhibit TLR4 dimerization. The formulation may be used to inhibit TLR4 signaling. The formulation may be used to inhibit IL-6 generation.

The formulation may be used to treat or prevent diseases which are mediated through the activation of TLR4 or the generation of IL-6. Examples of such disease include, but not limited to, sepsis; Ebola virus disease; Marburg virus disease; pain; septicemia including but not limited to endotoxemia; endotoxemia resulting from gram negative bacteremia with its accompanying symptoms of fever, generalized inflammation, disseminated intravascular coagulation, hypotension, acute renal failure, acute respiratory distress syndrome, adult respiratory distress syndrome (ARDS), hepatocellular destruction and/or cardiac failure; and various forms of septic shock including but not limited to endotoxic shock.

The formulation may be used to inhibit TNF-α generation. The formulation may be used to treat or prevent diseases which are mediated through the generation of TNF-α. Examples of such disease include, but not limited to, sepsis; Ebola virus disease; Marburg virus disease; pain; rheumatoid arthritis; psoriasis; diabetes; dyslipidemia including but not limited to hyperlipidemia, primary hyperlipidemia, hypercholesterolemia, familial combined hyperlipidemia, hyperlipoproteinemia, hypolipoproteinemia and hypertriglyceridemia; and osteoporosis.

Appropriate dosage and administration of the formulation may be determined by one of skill in the art, depending on age, weight and health conditions of subjects, a disease to be treated or prevented, administration route, etc.

The formulation is preferably administered parenterally, and more preferably administered intravenously.

The dosage form of the formulation may be injection or infusion.

The amount of the injection formulation to be administered eritoran basis may be 0.001 to 20 mg eritoran/kg body weight per dose, preferably 0.01 to 10 mg eritoran/kg body weight per dose. The injection formulation may be administered 1 to 6 times per day, preferably 1 to 3 times per day. The injection formulation may be administered over a period of 1 to 10 days, preferably 1 to 5 days.

The amount of the infusion formulation to be administered eritoran basis may be 0.001 to 10 mg eritoran/kg body weight/hour, preferably 0.003 to 5 mg eritoran/kg body weight/hour. The infusion formulation may be administered for 0.5 to 6 hours/day, preferably 1 to 3 hours/day. The infusion formulation may be administered over a period of 1 to 10 days, preferably 1 to 5 days.

The term "subject" refers to an animal, preferably a mammal, and more preferably a human, who is the object of the treatment or prevention. Examples of the mammal include, but not limited to, mice, rats, hamsters, gerbils, rabbits, guinea pigs, dogs, cats, sheep, goats, cows, horses, giraffes, platypuses, primates such as humans, monkeys, chimpanzees and apes. The subject is preferably a human.

<Production Method>

One embodiment relates to a method for producing the formulation comprising liposomes as defined above. Specifically, the method comprises:

preparing a solution comprising, based on all components of the liposomes to be used, 0.7 to 3.0 mol % of eritoran or a pharmaceutically acceptable salt thereof, 0.5 to 3.0 mol % of a PEGylated phospholipid and a solvent;

evaporating the solvent from the solution to form a thin film;

dispersing the thin film in a buffer solution to form a liquid dispersion; and extruding the liquid dispersion through a filter to form the formulation.

As to the components of the liposomes to be used in the preparing step and the amount thereof, the components of the liposome and the amount thereof, which are described in the above section <Formulation>, can be referred to.

Any solvent can be used in the preparing step as long as the solvent dissolves components of the liposome. Examples of the solvent include, but not limited to, halogenated hydrocarbons such as chloroform and dichloromethane, and alcohols such as methanol and ethanol. The solvent is preferably a combination of chloroform and methanol.

The dispersing step is preferably performed by sonication. The buffer solution preferably comprises a saccharide such as sucrose. The temperature of the buffer solution is preferably 50 to 90° C., and more preferably 60 to 80° C.

The filter used in the extruding step preferably comprises two or more filter members which are laid on top of one another. The number of the filter members is preferably 2 to 6, more preferably 3 to 5, and still more preferably 4. The filter members preferably have a different pore size, respectively. The pore size of the filter members is preferably 0.05 to 1.5 µm, more preferably 0.08 to 1.0 µm, and still more preferably 0.1 to 0.8 µm. When the number of the filter members is 4, the pore size of the each filter member is preferably 0.1 µm, 0.2 µm, 0.4 µm and 0.8 µm, respectively. The filtration in the extruding step is performed preferably two or more times, more preferably 3 to 7 times, and still more preferably 4 to 6 times.

The method may further comprise adjusting the pH of the formulation, which is formed in the extruding step, to preferably 6.2 to 6.8, and more preferably 6.4 to 6.6. The pH may be adjusted with an alkali metal hydroxide such as NaOH and KOH or an inorganic acid such as HCl. The formulation whose pH is adjusted may be sterilized through a sterilizing filter.

EXAMPLES

<Preparation of Formulation>
(Materials)

The following materials from the indicated sources were used in Examples: eritoran (from Eisai Co., Ltd.); cholesterol (Chol, from Wako Pure Chemical (Wako)); 1,2-distearoyl-sn-glycero-3-phosphocholine (DSPC, from Nippon Pure Chemical); 1,2-distearoyl-sn-glycero-3-phosphoethanolamine-N-[methoxy(polyethyleneglycol)-2000] (DSPE-PEG2000, from Genzyme); butylated hydroxyanisole (BHA, from Wako); chloroform (from Wako); methanol (from Wako); sucrose (from Wako); anhydrous $NaH_2PO_4$ (from Wako); 1N-HCl (from Wako); 1N-NaOH (from KANTO Chemical) and water purified by Milli-Q Gradient A10 (Merck Millipore).

(Apparatus)

The following equipment from the indicated sources were used in Examples: Balance: METTLER AT250 and PG503; pH Meter: HORIBA pH/ION METER D-53; Rotary Evaporator: EYELA N-1000; Digital Water Bath: EYELA SB-1000; Vacuum Pump: SATO VACUUM MACHINERY Oil Rotary Vacuum Pump SW-100.

Example 1

A formulation comprising the components listed in Table 1 was prepared.

TABLE 1

| Example 1: 2.5 mol % Eritoran, 2.5 mol % DSPE-PEG2000, 6 mol % Chol | | | |
|---|---|---|---|
| Material | mM | mol % | in 5 mL Batch |
| Eritoran | 1.00 | 2.50 | 7.01 mg* |
| Cholesterol | 2.40 | 6.00 | 4.64 mg |
| DSPC | 35.57 | 88.93 | 140.54 mg |
| DSPE-PEG2000 | 1.00 | 2.50 | 14.03 mg |
| BHA | 0.03 | 0.07 | 0.03 mg |
| Total | 40.00 | 100.00 | 166.24 mg |

*mg of eritoran as the tetra sodium salt

The following reagents were used in Example 1.
(1) 0.1N-NaOH

One mL of 1N-NaOH was put in 10 mL-volumetric flask and then was made up to the volume with the purified water.
(2) 0.1N-HCl One mL of 1N-HCl was put in 10 mL-volumetric flask and then was made up to the volume with the purified water.
(3) Sucrose Buffer Solution Twenty g of sucrose was weighed in a 200 mL-glass beaker and approximately 180 mL of the purified water was added. Then 24 mg of $NaH_2PO_4$ was added and pH value was adjusted to 6.5 by adding 0.1N-NaOH and 0.1N-HCl. The solution was put in 200 mL-volumetric flask and made up to the volume with the purified water.
(4) Chloroform/Methanol Mixture Fifty mL of chloroform and 100 mL of methanol were mixed in a glass bottle.
(5) Eritoran Solution Forty mg of eritoran was weighed out to a glass bottle and 10 mL of the chloroform/methanol mixture was added. Eritoran was dissolved completely with shaking.
(6) DSPC Solution Two point five g of DSPC was weighed out to a glass bottle and 60 mL of the chloroform/methanol mixture was added. DSPC was dissolved completely with shaking.
(7) Cholesterol Solution Ninety mg of cholesterol was weighed out to a glass bottle and 30 mL of the chloroform/methanol mixture was added. Cholesterol was dissolved completely with shaking.
(8) DSPE-PEG2000 Solution Five hundred mg of DSPE-PEG2000 was weighed out to a glass bottle and 20 mL of the chloroform/methanol mixture was added. DSPE-PEG2000 was dissolved completely with shaking.
(9) BHA Solution Four mg of BHA was weighed out to a glass bottle and 10 mL of the chloroform/methanol mixture was added. BHA was dissolved completely with shaking.
(1) Preparation of Thin Film For the preparation of the formulation indicated in Table 1, 1.75 mL of the eritoran solution, 3.37 mL of the DSPC solution, 1.55 mL of the cholesterol solution, 0.56 mL of the DSPE-PEG2000 solution, and 60 µL of the BHA solution were mixed in a 50-mL round bottom flask. After confirming that all of the components were completely dissolved, the solvent was removed by the rotary evaporator to make a thin film from the components. The round bottom flask was placed in vacuum chamber overnight to remove residual solvent.

(2) Preparation of Liquid Dispersion

The sucrose buffer solution was heated to 70° C. in water bath and 5 mL of the heated sucrose buffer solution was added to the round bottom flask containing the thin film. The mixture was sonicated in ultrasonic bath until the thin film was dispersed completely.

(3) Preparation of Formulation

The extruder was assembled with laying PC filters of pore size 0.1 µm, 0.2 µm, 0.4 µm, 0.8 µm on top of one another, and the circulating water bath was set to 70° C. The extruder was attached to a $N_2$ cylinder with regulator and pressure relief valve. The extruder assembly was allowed to heat up, and then it was loaded with the liquid dispersion. The extruder was closed and the liquid dispersion was allowed to equilibrate to 70° C. The $N_2$ cylinder line was opened and the $N_2$ pressure was slowly increased until a steady flow of the liquid dispersion was observed flowing from the outlet hose. Filtration steps were repeated 4 additional times. The filtrate from the 5th filtration was collected into a clean tube and the pH value of the filtrate was adjusted to 6.5 with 0.1N-NaOH and/or 0.1N-HCl after cooling to room temperature. The filtrate was sterilized using syringe filter (Whatman PES Filter Media with Polypropylene Housing, Pore Size 0.2 µm) and stored in refrigerator to avoid freezing until it was used for experiments. Thus obtained formulation was confirmed to comprise liposomes by Dynamic Light Scattering Analysis.

Example 2

A formulation comprising the components listed in Table 2 was prepared.

TABLE 2

Example 2: 1.0 mol % Eritoran, 2.5 mol % DSPE-PEG2000, 6 mol % Chol

| Material | mM | mol % | in 5 mL Batch |
| --- | --- | --- | --- |
| Eritoran | 1.00 | 1.00 | 7.01 mg* |
| Cholesterol | 6.00 | 6.00 | 11.60 mg |
| DSPC | 90.43 | 90.43 | 357.27 mg |
| DSPE-PEG2000 | 2.50 | 2.50 | 35.07 mg |
| BHA | 0.07 | 0.07 | 0.06 mg |
| Total | 100.00 | 100.00 | 411.01 mg |

*mg of eritoran as the tetra sodium salt

The following reagents were used in Example 2.

(1) 0.1N-NaOH

One mL of 1N-NaOH was put in 10 mL-volumetric flask and then was made up to the volume with the purified water.

(2) 0.1N-HCl

One mL of 1N-HCl was put in 10 mL-volumetric flask and then was made up to the volume with the purified water.

(3) Sucrose Buffer Solution

Twenty g of sucrose was weighed in a 200 mL-glass beaker and approximately 180 mL of the purified water was added. Then 24 mg of $NaH_2PO_4$ was added and pH value was adjusted to 6.5 by adding 0.1N-NaOH and 0.1N-HCl. The solution was put in 200 mL-volumetric flask and made up to the volume with the purified water.

(4) Chloroform/Methanol Mixture

Fifty mL of chloroform and 100 mL of methanol were mixed in a glass bottle.

(5) BHA Solution

Six mg of BHA was weighed out to a glass bottle and 10 mL of the chloroform/methanol mixture was added. BHA was dissolved completely with shaking.

(1) Preparation of Thin Film

For the preparation of the formulation indicated in Table 2, 6.7 mg of eritoran, 368.3 mg of DSPC, 11.9 mg of cholesterol, and 34.9 mg of DSPE-PEG2000 were weighed out to a 50-mL round bottom flask. Eight mL of chloroform and 3 mL of methanol was added and the flask was shaken gently. After confirming that all of the components were completely dissolved, 40 µL of the BHA solution was added. The solvent was removed by the rotary evaporator to make a thin film from the components. The round bottom flask was placed in vacuum chamber overnight to remove residual solvent.

(2) Preparation of Liquid Dispersion

The sucrose buffer solution was heated to 70° C. in water bath and 5 mL of the heated sucrose buffer solution was added to the round bottom flask containing the thin film. The mixture was sonicated in ultrasonic bath until the thin film was dispersed completely.

(3) Preparation of Formulation

The extruder was assembled with laying PC filters of pore size 0.1 µm, 0.2 µm, 0.4 µm, 0.8 µm on top of one another, and the circulating water bath was set to 70° C. The extruder was attached to a $N_2$ cylinder with regulator and pressure relief valve. The extruder assembly was allowed to heat up, and then it was loaded with the liquid dispersion. The extruder was closed and the liquid dispersion was allowed to equilibrate to 70° C. The $N_2$ cylinder line was opened and the $N_2$ pressure was slowly increased until a steady flow of the liquid dispersion was observed flowing from the outlet hose. Filtration steps were repeated 4 additional times. The filtrate from the 5th filtration was collected into a clean tube and the pH value of the filtrate was adjusted to 6.5 with 0.1N-NaOH and/or 0.1N-HCl after cooling to room temperature. The filtrate was sterilized using syringe filter (Whatman PES Filter Media with Polypropylene Housing, Pore Size 0.2 µm) and stored in refrigerator to avoid freezing until it was used for experiments. Thus obtained formulation was confirmed to comprise liposomes by Dynamic Light Scattering Analysis.

Example 3

A formulation comprising the components listed in Table 3 was prepared.

TABLE 3

Example 3: 1 mol % Eritoran, 1 mol % DSPE-PEG2000, 6 mol % Chol

| Material | mM | mol % | in 5 mL Batch |
| --- | --- | --- | --- |
| Eritoran | 1.00 | 1.00 | 7.01 mg* |
| Cholesterol | 6.00 | 6.00 | 11.60 mg |
| DSPC | 91.93 | 91.93 | 363.19 mg |
| DSPE-PEG2000 | 1.00 | 1.00 | 14.03 mg |
| BHA | 0.07 | 0.07 | 0.16 mg |
| Total | 100.00 | 100.00 | 395.99 mg |

*mg of eritoran as the tetra sodium salt

The following reagents were used in Example 3.

(1) 0.1N-NaOH

One mL of 1N-NaOH was put in 10 mL-volumetric flask and then was made up to the volume with the purified water.

(2) 0.1N-HCl

One mL of 1N-HCl was put in 10 mL-volumetric flask and then was made up to the volume with the purified water.

(3) Sucrose Buffer Solution

Twenty g of sucrose was weighed in a 200 mL-glass beaker and approximately 180 mL of the purified water was added. Then 24 mg of $NaH_2PO_4$ was added and pH value was adjusted to 6.5 by adding 0.1N-NaOH and 0.1N-HCl. The solution was put in 200 mL-volumetric flask and made up to the volume with the purified water.

(4) Chloroform/Methanol Mixture

Fifty mL of chloroform and 100 mL of methanol were mixed in a glass bottle.

(5) Eritoran Solution

Sixty mg of eritoran was weighed out to a glass bottle and 10 mL of the chloroform/methanol mixture was added. Eritoran was dissolved completely with shaking.

(6) DSPC Solution

One point two g of DSPC was weighed out to a glass bottle and 50 mL of the chloroform/methanol mixture was added. DSPC was dissolved completely with shaking.

(7) Cholesterol Solution

Fifty mg of cholesterol was weighed out to a glass bottle and 25 mL of the chloroform/methanol mixture was added. Cholesterol was dissolved completely with shaking.

(8) DSPE-PEG2000 Solution

Four hundred and fifty mg of DSPE-PEG2000 was weighed out to a glass bottle and 20 mL of the chloroform/methanol mixture was added. DSPE-PEG2000 was dissolved completely with shaking.

(9) BHA Solution

Four mg of BHA was weighed out to a glass bottle and 10 mL of the chloroform/methanol mixture was added. BHA was dissolved completely with shaking.

(1) Preparation of Thin Film

For the preparation of the formulation indicated in Table 3, 1.17 mL of the eritoran solution, 12.13 mL of the DSPC solution, 5.8 mL of the cholesterol solution, 0.62 mL of the DSPE-PEG2000 solution, and 400 µL of the BHA solution were mixed in a 50-mL round bottom flask. After confirming that all of the components were completely dissolved, the solvent was removed by the rotary evaporator to make a thin film from the components. The round bottom flask was placed in vacuum chamber overnight to remove residual solvent.

(2) Preparation of Liquid Dispersion

The sucrose buffer solution was heated to 70° C. in water bath and 5 mL of the heated sucrose buffer solution was added to the round bottom flask containing the thin film. The mixture was sonicated in ultrasonic bath until the thin film was dispersed completely.

(3) Preparation of Formulation

The extruder was assembled with laying PC filters of pore size 0.1 µm, 0.2 µm, 0.4 µm, 0.8 µm on top of one another, and the circulating water bath was set to 70° C. The extruder was attached to a $N_2$ cylinder with regulator and pressure relief valve. The extruder assembly was allowed to heat up, and then it was loaded with the liquid dispersion. The extruder was closed and the liquid dispersion was allowed to equilibrate to 70° C. The $N_2$ cylinder line was opened and the $N_2$ pressure was slowly increased until a steady flow of the liquid dispersion was observed flowing from the outlet hose. Filtration steps were repeated 4 additional times. The filtrate from the 5th filtration was collected into a clean tube and the pH value of the filtrate was adjusted to 6.5 with 0.1N-NaOH and/or 0.1N-HCl after cooling to room temperature. The filtrate was sterilized using syringe filter (Whatman PES Filter Media with Polypropylene Housing, Pore Size 0.2 µm) and stored in refrigerator to avoid freezing until it was used for experiments. Thus obtained formulation was confirmed to comprise liposomes by Dynamic Light Scattering Analysis.

Example 4

A formulation comprising the components listed in Table 4 was prepared.

TABLE 4

| Example 4: 2.5 mol % Eritoran, 1 mol % DSPE-PEG2000, 6 mol % Chol | | | |
|---|---|---|---|
| Material | mM | mol % | in 5 mL Batch |
| Eritoran | 1.00 | 2.50 | 7.01 mg* |
| Cholesterol | 2.40 | 6.00 | 4.64 mg |
| DSPC | 36.17 | 90.43 | 142.91 mg |
| DSPE-PEG2000 | 0.40 | 1.00 | 5.61 mg |
| BHA | 0.03 | 0.07 | 0.03 mg |
| Total | 40.00 | 100.00 | 160.19 mg |

*mg of eritoran as the tetra sodium salt

The following reagents were used in Example 4.

(1) 0.1N-NaOH

One mL of 1N-NaOH was put in 10 mL-volumetric flask and then was made up to the volume with the purified water.

(2) 0.1N-HCl

One mL of 1N-HCl was put in 10 mL-volumetric flask and then was made up to the volume with the purified water.

(3) Sucrose Buffer Solution

Twenty g of sucrose was weighed in a 200 mL-glass beaker and approximately 180 mL of the purified water was added. Then 24 mg of $NaH_2PO_4$ was added and pH value was adjusted to 6.5 by adding 0.1N-NaOH and 0.1N-HCl. The solution was put in 200 mL-volumetric flask and made up to the volume with the purified water.

(4) Chloroform/Methanol Mixture

Fifty mL of chloroform and 100 mL of methanol were mixed in a glass bottle.

(5) Eritoran Solution

Fifty mg of eritoran was weighed out to a glass bottle and 10 mL of the chloroform/methanol mixture was added. Eritoran was dissolved completely with shaking.

(6) DSPC Solution

Six hundred mg of DSPC was weighed out to a glass bottle and 10 mL of the chloroform/methanol mixture was added. DSPC was dissolved completely with shaking.

(7) Cholesterol Solution

Twenty-five mg of cholesterol was weighed out to a glass bottle and 10 mL of chloroform was added. Cholesterol was dissolved completely with shaking.

(8) DSPE-PEG2000 Solution

Eighty mg of DSPE-PEG2000 was weighed out to a glass bottle and 10 mL of the chloroform/methanol mixture was added. DSPE-PEG2000 was dissolved completely with shaking.

(9) BHA Solution

Six mg of BHA was weighed out to a glass bottle and 10 mL of the chloroform/methanol mixture was added. BHA was dissolved completely with shaking.

(1) Preparation of Thin Film

For the preparation of the formulation indicated in Table 4, 1.40 mL of the eritoran solution, 2.38 mL of the DSPC solution, 1.86 mL of the cholesterol solution, 0.70 mL of the DSPE-PEG2000 solution, and 40 μL of the BHA solution were mixed in a 50-mL round bottom flask. After confirming that all of the components were completely dissolved, the solvent was removed by the rotary evaporator to make a thin film from the components. The round bottom flask was placed in vacuum chamber overnight to remove residual solvent.

(2) Preparation of Liquid Dispersion

The sucrose buffer solution was heated to 70° C. in water bath and 5 mL of the heated sucrose buffer solution was added to the round bottom flask containing the thin film. The mixture was sonicated in ultrasonic bath until the thin film was dispersed completely.

(3) Preparation of Formulation

The extruder was assembled with laying PC filters of pore size 0.1 μm, 0.2 μm, 0.4 μm, 0.8 μm on top of one another, and the circulating water bath was set to 70° C. The extruder was attached to a $N_2$ cylinder with regulator and pressure relief valve. The extruder assembly was allowed to heat up, and then it was loaded with the liquid dispersion. The extruder was closed and the liquid dispersion was allowed to equilibrate to 70° C. The $N_2$ cylinder line was opened and the $N_2$ pressure was slowly increased until a steady flow of the liquid dispersion was observed flowing from the outlet hose. Filtration steps were repeated 4 additional times. The filtrate from the 5th filtration was collected into a clean tube and the pH value of the filtrate was adjusted to 6.5 with 0.1N-NaOH and/or 0.1N-HCl after cooling to room temperature. The filtrate was sterilized using syringe filter (Whatman PES Filter Media with Polypropylene Housing, Pore Size 0.2 μm) and stored in refrigerator to avoid freezing until it was used for experiments. Thus obtained formulation was confirmed to comprise liposomes by Dynamic Light Scattering Analysis.

Examples 5 to 8

Formulations comprising the components listed in Tables 5 and 6 were prepared.

TABLE 5

| Material | mM | mol % | in 5 mL Batch |
|---|---|---|---|
| Example 5: 2.5 mol % Eritoran, 2.5 mol % DSPE-PEG2000, 0 mol % Chol | | | |
| Eritoran | 1.00 | 2.50 | 7.01 mg* |
| Cholesterol | — | — | — |
| DSPC | 37.97 | 94.93 | 150.02 mg |
| DSPE-PEG2000 | 1.00 | 2.50 | 14.03 mg |
| BHA | 0.03 | 0.07 | 0.03 mg |
| Total | 40.00 | 100.00 | 171.08 mg |
| Example 6: 2.5 mol % Eritoran, 2.5 mol % DSPE-PEG2000, 30 mol % Chol | | | |
| Eritoran | 1.00 | 2.50 | 7.01 mg* |
| Cholesterol | 12.00 | 30.00 | 23.20 mg |
| DSPC | 25.97 | 64.93 | 102.61 mg |
| DSPE-PEG2000 | 1.00 | 2.50 | 14.03 mg |
| BHA | 0.03 | 0.07 | 0.03 mg |
| Total | 40.00 | 100.00 | 146.87 mg |

*mg of eritoran as the tetra sodium salt

TABLE 6

| Material | mM | mol % | in 5 mL Batch |
|---|---|---|---|
| Example 7: 0.5 mol % Eritoran, 1 mol % DSPE-PEG2000, 6 mol % Chol | | | |
| Eritoran | 0.25 | 0.50 | 1.75 mg* |
| Cholesterol | 3.00 | 6.00 | 5.80 mg |
| DSPC | 46.21 | 92.43 | 182.58 mg |
| DSPE-PEG2000 | 0.50 | 1.00 | 7.01 mg |
| BHA | 0.04 | 0.07 | 0.03 mg |
| Total | 50.00 | 100.00 | 197.18 mg |
| Example 8: 0.5 mol % Eritoran, 2.5 mol % DSPE-PEG2000, 6 mol % Chol | | | |
| Eritoran | 0.25 | 0.5 | 1.75 mg* |
| Cholesterol | 3.00 | 6.00 | 5.80 mg |
| DSPC | 45.46 | 90.93 | 179.62 mg |
| DSPE-PEG2000 | 1.25 | 2.50 | 17.53 mg |
| BHA | 0.04 | 0.07 | 0.03 mg |
| Total | 50.00 | 100.00 | 204.74 mg |

*mg of eritoran as the tetra sodium salt

The following reagents were used in Examples 5 to 8.

(1) 0.1N-NaOH

One mL of 1N-NaOH was put in 10 mL-volumetric flask and then was made up to the volume with the purified water.

(2) 0.1N-HCl

One mL of 1N-HCl was put in 10 mL-volumetric flask and then was made up to the volume with the purified water.

(3) Sucrose Buffer Solution

Twenty g of sucrose was weighed in a 200 mL-glass beaker and approximately 180 mL of the purified water was added. Then 24 mg of $NaH_2PO_4$ was added and pH value was adjusted to 6.5 by adding 0.1N-NaOH and 0.1N-HCl. The solution was put in 200 mL-volumetric flask and made up to the volume with the purified water.

(4) Chloroform/Methanol Mixture

Fifty mL of chloroform and 100 mL of methanol were mixed in a glass bottle.

(5) Eritoran Solution

Five mg of eritoran was weighed out to a glass bottle and 5 mL of the chloroform/methanol mixture was added. Eritoran was dissolved completely with shaking.

(6) DSPC Solution

Seven hundred and fifty mg of DSPC was weighed out to a glass bottle and 50 mL of the chloroform/methanol mixture was added. DSPC was dissolved completely with shaking.

(7) Cholesterol Solution

Forty-five mg of cholesterol was weighed out to a glass bottle and 10 mL of chloroform was added. Cholesterol was dissolved completely with shaking.

(8) DSPE-PEG2000 Solution

Sixty-five mg of DSPE-PEG2000 was weighed out to a glass bottle and 5 mL of the chloroform/methanol mixture was added. DSPE-PEG2000 was dissolved completely with shaking.

(9) BHA Solution

Six mg of BHA was weighed out to a glass bottle and 10 mL of the chloroform/methanol mixture was added. BHA was dissolved completely with shaking.

(1) Preparation of Thin Film

For the preparation of the formulation of Example 5 indicated in Table 5, 1.39 mL of the eritoran solution, 10.0 mL of the DSPC solution, 1.07 mL of the DSPE-PEG2000 solution, and 40 μL of the BHA solution were mixed in a 50-mL round bottom flask.

For the preparation of the formulation of Example 6 indicated in Table 5, 1.39 mL of the eritoran solution, 4.98 mL of cholesterol solution, 6.84 mL of the DSPC solution, 1.07 mL of the DSPE-PEG2000 solution, and 40 µL of the BHA solution were mixed in a 50-mL round bottom flask.

For the preparation of the formulation of Example 7 indicated in Table 6, 0.35 mL of the eritoran solution, 1.25 mL of cholesterol solution, 12.18 mL of the DSPC solution, 0.54 mL of the DSPE-PEG2000 solution, and 50 µL of the BHA solution were mixed in a 50-mL round bottom flask.

For the preparation of the formulation of Example 8 indicated in Table 6, 0.35 mL of the eritoran solution, 1.25 mL of cholesterol solution, 11.98 mL of the DSPC solution, 1.34 mL of the DSPE-PEG2000 solution, and 50 µL of the BHA solution were mixed in a 50-mL round bottom flask.

After confirming that all of the components were completely dissolved, the solvent of each flask was removed by the rotary evaporator to make a thin film from the components. The round bottom flasks were placed in vacuum chamber overnight to remove residual solvent.

(2) Preparation of Liquid Dispersion

The sucrose buffer solution was heated to 70° C. in water bath and 5 mL of the heated sucrose buffer solution was added to each flask containing the thin film. The mixture was sonicated in ultrasonic bath until the thin film was dispersed completely.

(3) Preparation of Formulation

The extruder was assembled with laying PC filters of pore size 0.1 µm, 0.2 µm, 0.4 µm, 0.8 µm on top of one another, and the circulating water bath was set to 70° C. The extruder was attached to a $N_2$ cylinder with regulator and pressure relief valve. The extruder assembly was allowed to heat up, and then it was loaded with the liquid dispersion. The extruder was closed and the liquid dispersion was allowed to equilibrate to 70° C. The $N_2$ cylinder line was opened and the $N_2$ pressure was slowly increased until a steady flow of the liquid dispersion was observed flowing from the outlet hose. Filtration steps were repeated 4 additional times. The filtrate from the 5th filtration was collected into a clean tube and the pH value of the filtrate was adjusted to 6.5 with 0.1N-NaOH and/or 0.1N-HCl after cooling to room temperature. The filtrate was sterilized using syringe filter (Whatman PES Filter Media with Polypropylene Housing, Pore Size 0.2 µm) and stored in refrigerator to avoid freezing until it was used for experiments. Thus obtained formulations were confirmed to comprise liposomes by Dynamic Light Scattering Analysis.

Examples 9 to 26

Formulations comprising the components listed in Table 7 were prepared.

TABLE 7

| Example No. | mol % | | | | |
|---|---|---|---|---|---|
| | Eritoran | DSPC | Chol | DSPE-PEG2000 | BHA |
| Example 9 | 1 | 87.929 | 6 | 5 | 0.071 |
| Example 10 | 2.5 | 86.429 | 6 | 5 | 0.071 |
| Example 11 | 5 | 83.929 | 6 | 5 | 0.071 |
| Example 12 | 7.5 | 81.429 | 6 | 5 | 0.071 |
| Example 13 | 5 | 86.429 | 6 | 2.5 | 0.071 |
| Example 14 | 7.5 | 83.929 | 6 | 2.5 | 0.071 |
| Example 15 | 5 | 87.929 | 6 | 1 | 0.071 |
| Example 16 | 5 | 88.929 | 6 | 0 | 0.071 |
| Example 17 | 5 | 81.429 | 6 | 7.5 | 0.071 |
| Example 18 | 7.5 | 78.929 | 6 | 7.5 | 0.071 |
| Example 19 | 1 | 75.429 | 6 | 17.5 | 0.071 |
| Example 20 | 5 | 71.429 | 6 | 17.5 | 0.071 |
| Example 21 | 1 | 85.429 | 6 | 7.5 | 0.071 |
| Example 22 | 2.5 | 83.929 | 6 | 7.5 | 0.071 |
| Example 23 | 1 | 92.929 | 6 | 0 | 0.071 |
| Example 24 | 0 | 91.429 | 6 | 2.5 | 0.071 |
| Example 25 | 0 | 88.929 | 6 | 5 | 0.071 |
| Example 26 | 0 | 86.429 | 6 | 7.5 | 0.071 |

The formulations of Examples 9 to 26 were prepared in almost the same procedure as in Example 1. The eritoran concentration of the formulations in Table 7 was approximately 1 mM. Total lipid concentration of the formulations without eritoran (Examples 24 to 26) was approximately 100 mM.

<Dynamic Light Scattering Analysis>

The formulations of Examples 1 to 26 were analyzed by dynamic light scattering (DLS) to determine an average particle size (Z-ave) and a polydispersity index (PdI). The following settings were used for the DLS analysis.

(Experimental Procedure)
System: Zetasizer Nano-ZS (Malvern Panalytical)
Measurement conditions:
Reflective Index of Sample: 1.45
Adsorption Rate of Sample: 0.01
Dispersion Media: Milli-Q water
Reflective Index of Dispersion Media: 1.330
Viscosity of Dispersion Media (cP): 1.0031
Measurement Temperature: 20° C.
Pre-Incubation Time: 5 min.
Measurement Time: 60 sec., 3 times
Measurement Position (Distance): 4.65 mm
Sample Preparation:
Fifty microliter of sample into 5 mL of Milli-Q water (Result of DLS Analysis)

The Z-ave and PdI values of each formulation were summarized in Table 8. The formulations other than those of Examples 18 to 20 had Z-ave of 100 nm or more, so it was considered that eritoran-containing liposomes were formed in these formulations. The formulations other than those of Examples 18 to 22 and 26 had PdI of 0.2 or less, so it was considered that particle size distribution is sufficiently controlled in these formulations. The PdI of the formulations comprising eritoran of Examples 18 to 22 (i.e. more than 0.2) shows a possibility of issue on uniformity as a fine particle formulation of eritoran.

TABLE 8

| Example No | Z-ave (nm) | PdI |
|---|---|---|
| Example 1 | 117 | 0.11 |
| Example 2 | 106.1 | 0.091 |
| Example 3 | 112.5 | 0.185 |
| Example 4 | 120.3 | 0.095 |
| Example 5 | 116.5 | 0.046 |
| Example 6 | 119.7 | 0.034 |
| Example 7 | 112.2 | 0.05 |
| Example 8 | 114.3 | 0.04 |
| Example 9 | 107.6 | 0.091 |
| Example 10 | 118.5 | 0.095 |
| Example 11 | 119.6 | 0.098 |
| Example 12 | 100.4 | 0.188 |
| Example 13 | 118.4 | 0.092 |
| Example 14 | 104.8 | 0.126 |

TABLE 8-continued

| Example No | Z-ave (nm) | PdI |
|---|---|---|
| Example 15 | 121.3 | 0.095 |
| Example 16 | 107.9 | 0.145 |
| Example 17 | 104.4 | 0.195 |
| Example 18 | 49.8 | 0.243 |
| Example 19 | 62.7 | 0.477 |
| Example 20 | 44.2 | 0.337 |
| Example 21 | 110.9 | 0.253 |
| Example 22 | 109 | 0.209 |
| Example 23 | 109.3 | 0.126 |
| Example 24 | 120.4 | 0.092 |
| Example 25 | 119.9 | 0.068 |
| Example 26 | 104.8 | 0.209 |

<Micellized Eritoran and Placebo Used In Vivo and In Vitro Assays>

Micellized eritoran and placebo used in vivo and in vitro assays were prepared from freeze-dried powder in a vial. Micellized eritoran vial contains eritoran (as tetra sodium 4.0 [Na] salt basis) 7.46 mg, lactose monohydorate, and butylated hydroxyanisole. Sodium hydroxide and phosphoric acid are also contained quantum sufficit in the micellized eritoran vial. Placebo vial contains lactose monohydrate. Dibasic sodium phosphate heptahydrate, monobasic sodium phosphate monohydrate, and sodium hydroxide are also contained quantum sufficit in the placebo vial. Each vial was reconstituted with 3.0 ml of sterile water for injection (solution is 2.33 mg/ml or 1.66 mM). Reconstituted micellized eritoran was diluted by the reconstituted placebo solution to prepare appropriate concentration.

<In Vivo Efficacy of Formulations of Examples>

In vivo efficacy of the formulations as prepared in Examples 1 to 26 were examined through mouse studies. C57BL/6NCrl (Charles River Laboratories) female mice with body weight of about 20 g/mouse were used, with 4 mice/group. Animals were i.v. injected with 9.1 mg/kg micellized eritoran or the formulations of Examples at time of 2 hours prior to LPS from *Escherichia coli* O111:B4 (with 0.5 μg/head, Cat #201, List Biological Laboratories, Inc.) administration via i.p. Two groups of mice were injected with the same volume of sucrose buffer and placebo as the formulation's mock control and micellized eritoran control, respectively. The animals were harvested for cytokine measurement in 2 hours after LPS injection and plasma were collected (from abdominal vein under anesthesia) in EDTA/3K tubes (Cat #499388, Greiner Bio-One GmbH). IL-6 cytokine was measured according to ELISA kit protocol (Mouse IL-6 ELISA Set, Cat #555240; Reagent Set B pH9.5, Cat #550534, BD Biosciences) except for below procedures. Capture antibody was diluted in Carbonate-bicarbonate buffer (with 1 cap in 50 ml Milli-Q water, Cat # C3041-100CAP, Sigma-Aldrich Corporation) as a coating buffer. Wells were washed with phosphate-buffered saline (Cat # P3563-10PAK, Sigma-Aldrich Corporation) by plate-washer (ELx405 select, BioTek Instruments, Inc.) at each step. To remove remained wash buffer, plate was centrifuged at 4,000 rpm for 1 min with up-side down at each step (HITACH CF16RXII; rotor: T5S32-0049). Absorption spectrophotometer was used to determine the optical density of each well (SpectraMax 190, Molecular Devices, LLC). Optical densities of duplicated wells were averaged, and standard curve was generated with a four parameter logistic (4-PL) curve-fit using SoftMax Pro 6.5.1 (Build number 219831, Molecular Devices, LLC). Plot and Median value with interquartile range were rendered with GraphPad Prism 7.02 (GraphPad software, Inc.). A part of the results is shown in FIG. 1 and further results are shown in Table 9. These results show that eritoran-containing liposomes inhibit IL-6 generation, compared with the micellized eritoran.

TABLE 9

| Example | IL-6 level on regular concentration (% of control) |
|---|---|
| Example 1 | 11.54 |
| Example 2 | 12.69 |
| Example 3 | 9.74 |
| Example 4 | 11.13 |
| Example 5 | 5.54 |
| Example 6 | 8.46 |
| Example 9 | 11.81 |
| Example 10 | 2.59 |
| Example 11 | 6.52 |
| Example 12 | 6.55 |
| Example 13 | 9.74 |
| Example 14 | 15.84 |
| Example 15 | 17.33 |
| Example 16 | 13.60 |
| Example 17 | 4.88 |
| Example 18 | 6.01 |
| Example 20 | 82.23 |
| Example 21 | 7.63 |
| Example 22 | 2.39 |
| Example 23 | 8.95 |
| Example 24 | 91.08 |
| Example 25 | 69.84 |
| Example 26 | 85.27 |
| Micellized eritoran | 59.26 |

<In vivo Screening Assay of Formulations of Examples>

Screening assay to narrow down superior formulations in Examples 1 to 26 was studied by partially modifying the protocol of the above assay ("In vivo Efficacy of Formulations of Examples"). Animals of the same condition were i.v. injected with 1.1375 mg/kg formulations of Examples diluted (8-fold) with sucrose buffer, also using a control, at time of 2 hours prior to LPS from *Escherichia coli* O111:B4 administration via i.p. The animals were harvested for cytokine measurement in 2 hours after LPS injection and plasma were collected (from abdominal vein under anesthesia) in EDTA/3K tubes. IL-6 cytokine was measured with the same procedure of the above assay ("In vivo Efficacy of Formulations of Examples"). A part of the results is shown in FIGS. 2-1, 2-2 and 2-3.

FIG. 2-1 shows that Diluted Example 1 inhibited 78.8% of IL-6 generation compared to mock control (median values of IL-6 concentration in mock group and Diluted Example 1 group were 2851.8 pg/ml and 606.0 pg/ml, respectively; line indicates median value with interquartile range). IL-6 generation-inhibiting activity was not observed in Diluted Example 11 and Diluted Example 13 (median values of IL-6 concentration in Diluted Example 11 and Diluted Example 13 groups were 3203.0 pg/ml and 4104.6 pg/ml, respectively).

FIGS. 2-2 and 2-3 show that the inhibition on this condition was also observed for Diluted Example 2, Diluted Example 3, Diluted Example 4, and Diluted Example 5 groups (median values of IL-6 concentration in mock control, Diluted Example 2, Diluted Example 3, and Diluted Example 4 groups were 2605.8 pg/ml, 390.9 pg/ml, 357.8 pg/ml, 626.3 pg/ml, respectively). Diluted Example 5, a cholesterol-modified formulation of Example 1, also showed a high IL-6 generation-inhibiting activity (96.7%, median values of IL-6 concentration in mock group and Example 5 group were 2812.1 pg/ml and 92.1 pg/ml, respectively).

Summary for all diluted formulations is shown in Table 10.

TABLE 10

| Diluted | IL-6 level on low concentration (% of control) | |
|---|---|---|
| Example | 1st assay | 2nd assay |
| Example 1 | 21.25 | 26.26 |
| Example 2 | 15.00 | 39.69 |
| Example 3 | 13.73 | 42.66 |
| Example 4 | 24.03 | 51.43 |
| Example 5 | 0.98 | 3.27 |
| Example 6 | 271.35 | 75.56 |
| Example 7 | 141.36 | — |
| Example 8 | 76.83 | — |
| Example 9 | 119.18 | — |
| Example 10 | 14.26 | 63.96 |
| Example 11 | 112.32 | 37.10 |
| Example 12 | 70.86 | 60.01 |
| Example 13 | 143.93 | — |
| Example 14 | 176.94 | — |
| Example 15 | 231.98 | — |
| Example 16 | 102.86 | — |
| Example 17 | 108.65 | — |
| Example 18 | 47.25 | 104.81 |
| Example 20 | 129.72 | — |
| Example 21 | 95.63 | — |
| Example 22 | 101.21 | — |
| Example 23 | 190.15 | — |

<Human HDL Inactivation Assay>

Influence of high-density lipoprotein (HDL) for the formulations of Examples was evaluated by following protocol. The formulations were diluted to 50 μM with saline (Cat #3311401A3111, Otsuka Pharmaceutical Co., Ltd.), and mixed with 1 mg/ml of human HDL (Cat # LP3-5MG, Merck KGaA). The mixed formulations were incubated at 37° C. for 18 hours. Healthy human whole blood was prepared with EDTA/2K test tube (VENOJECT (Registered Trademark), Cat # VP-H100K, TERUMO CORPORATION). The mixed formulations were mixed with 4-fold volumes of whole blood containing 10 ng/ml of LPS as a final concentration. After incubation at 37° C. for 3 hours, supernatant was prepared by centrifugation (1,000× g for 5 min at 4° C.). TNF-α was measured by ELISA (Cat # STA00C, R&D Systems). ELISA assay was conducted according to attached instruction manual. Wells were washed by plate-washer (ELx405 select, BioTek Instruments, Inc.) at each step. To remove remained wash buffer, plate was centrifuged at 4,000 rpm for 1 min with up-side down at each step (IIITACII CF16RXII; rotor: T5S32-0049). Absorption spectrophotometer was used to determine the optical density of each well (SpectraMax 190, Molecular Devices, LLC). Optical densities of duplicated wells were averaged, and standard curve was generated with a four parameter logistic (4-PL) curve-fit using SoftMax Pro 6.5.1 (Build number 219831, Molecular Devices, LLC). Plot and Median value with interquartile range were rendered with GraphPad Prism 7.02 (GraphPad software, Inc.). The results are shown in Table 11 and FIG. 3. These results show that the formulations of Examples 1 to 4 maintain their activities even in the presence of human HDL.

TABLE 11

| | PBS ctrl | Micellized eritoran | Example 1 | Example 2 | Example 3 | Example 4 |
|---|---|---|---|---|---|---|
| TNF-α concentration (pg/ml) | 6108.0 | 4351.8 | 210.3 | 437.2 | 273.7 | 215.1 |
| TNF-α level (% of control) | 100.0 | 71.2 | 3.4 | 7.2 | 4.5 | 3.5 |

The invention claimed is:

1. A formulation comprising liposomes, wherein the liposomes comprise, based on the liposome, 0.7 to 3.0 mol % of eritoran or a pharmaceutically acceptable salt thereof, a PEGylated phospholipid and 0 to 10 mol % of a sterol, wherein the molar ratio range of the eritoran or a pharmaceutically acceptable salt thereof and the PEGylated phospholipid is 1:0.4 to 1:2.5.

2. The formulation according to claim 1, wherein the pharmaceutically acceptable salt is tetrasodium salt.

3. The formulation according to claim 1, wherein the liposomes comprise, based on the liposome, 1.0 mol % of eritoran or a pharmaceutically acceptable salt thereof and 1.0 to 2.5 mol % of a PEGylated phospholipid.

4. The formulation according to claim 1, wherein the PEGylated phospholipid is 1,2-distearoyl-sn-glycero-3-phosphoethanolamine-N-[methoxy(polyethylene glycol)-2000].

5. The formulation according to claim 4, wherein the liposomes comprise, based on the liposome, 1.0 mol % of eritoran or a pharmaceutically acceptable salt thereof and 1.0 mol % of 1,2-distearoyl-sn-glycero-3-phosphoethanolamine-N-[methoxy(polyethylene glycol)-2000].

6. The formulation according to claim 4, wherein the liposomes comprise, based on the liposome, 1.0 mol % of eritoran or a pharmaceutically acceptable salt thereof and 2.5 mol % of 1,2-distearoyl-sn-glycero-3-phosphoethanolamine-N-[methoxy(polyethylene glycol)-2000].

7. The formulation according to claim 4, wherein the liposomes comprise, based on the liposome, 2.5 mol % of eritoran or a pharmaceutically acceptable salt thereof and 1.0 mol % of 1,2-distearoyl-sn-glycero-3-phosphoethanolamine-N-[methoxy(polyethylene glycol)-2000].

8. The formulation according to claim 4, wherein the liposomes comprise, based on the liposome, 2.5 mol % of eritoran or a pharmaceutically acceptable salt thereof and 2.5 mol % of 1,2-distearoyl-sn-glycero-3-phosphoethanolamine-N-[methoxy(polyethylene glycol)-2000].

9. The formulation according to claim 1, wherein the liposomes further comprise a phosphatidylcholine.

10. The formulation according to claim 9, wherein the phosphatidylcholine is distearoyl phosphatidyl choline.

11. The formulation according to claim 1, wherein the liposomes further comprise an antioxidant.

12. The formulation according to claim 11, wherein the antioxidant is butylated hydroxyanisole.

13. The formulation according to claim 1, wherein the sterol is cholesterol.

14. The formulation according to claim 1, wherein the liposomes do not comprise the sterol.

15. The formulation according to claim 1, wherein the liposomes have an average particle size between 100 to 120 nm, as measured by Dynamic Light Scattering (DLS).

16. The formulation according to claim 1, wherein the liposomes have a polydispersity index of 0.20 or less.

17. A method for producing a formulation comprising liposomes, comprising:

preparing a solution comprising, based on all components of the liposomes to be used, 0.7 to 3.0 mol % of eritoran or a pharmaceutically acceptable salt thereof, a PEGylated phospholipid, 0 to 10 mol % of a sterol and a solvent, wherein the molar ratio range of the eritoran or a pharmaceutically acceptable salt thereof and the PEGylated phospholipid is 1:0.4 to 1:2.5;

evaporating the solvent from the solution to form a thin film;

dispersing the thin film in a buffer solution to form a liquid dispersion; and extruding the liquid dispersion through a filter to form the formulation.

18. The method according to claim 17, wherein the solution further comprises a phosphatidylcholine and an antioxidant.

19. The method according to claim 17, wherein the solvent is a combination of chloroform and methanol.

20. The method according to claim 17, wherein the dispersing step is performed by sonication.

21. The method according to claim 17, wherein the method further comprises adjusting the pH of the formulation formed in the extruding step to 6.2 to 6.8.

* * * * *